United States Patent
Kato et al.

(10) Patent No.: US 6,638,951 B1
(45) Date of Patent: Oct. 28, 2003

(54) BENZAMIDE DERIVATIVES AND DRUGS CONTAINING THE SAME

(75) Inventors: Hideo Kato, Fukui (JP); Noriyuki Kado, Fukui (JP); Jun Sakaguchi, Fukui (JP)

(73) Assignee: Hokuriku Seiyaku Co., Ltd., Fukui (JP)

( * ) Notice: Subject to any disclaimer, the term of this patent is extended or adjusted under 35 U.S.C. 154(b) by 0 days.

(21) Appl. No.: 09/869,338

(22) PCT Filed: Feb. 2, 2000

(86) PCT No.: PCT/JP00/00560

§ 371 (c)(1),
(2), (4) Date: Nov. 8, 2001

(87) PCT Pub. No.: WO00/46201

PCT Pub. Date: Aug. 10, 2000

(30) Foreign Application Priority Data

Feb. 4, 1999 (JP) ............................................ 11/27030

(51) Int. Cl.[7] ..................... A61K 31/445; C07D 211/92
(52) U.S. Cl. ........................................ 514/329; 546/224
(58) Field of Search ........................... 514/329; 546/224

(56) References Cited

U.S. PATENT DOCUMENTS

| | | | |
|---|---|---|---|
| 4,877,780 A | 10/1989 | Vega-Noverola et al. | ... 514/161 |
| 5,395,832 A | 3/1995 | Ito et al. | ..................... 514/214 |
| 5,500,422 A | 3/1996 | Ito et al. | ..................... 514/212 |

FOREIGN PATENT DOCUMENTS

| | | | |
|---|---|---|---|
| EP | 0640601 | 1/1995 | ................ 514/214 |
| JP | 5-262724 | 10/1993 | ................ 514/214 |
| JP | 11292846 | 10/1999 | ................ 514/214 |

OTHER PUBLICATIONS

Zen Itho, "An Extraluminal Strain Gage Force Transducer Its Construction and Implantation", Jap. J. Smooth Muscle Res., vol. 13, pp. 33–43 (1976).

Zen Itoh et al., "An Extraluminal Force Transducer for Recording Contractile Activity of the Gastrointestinal Smooth Muscle in the Conscious Dogs: Its Construction and Implantation", Gastroenterologia Japonica, Vol 12, No. 4, pp. 18–26 (1977).

Jun Sakaguchi et al., "Synthesis and Gastrointestinal Prokinetic Activity of Novel Benzamide Derivatives with Amphoteric Side Chains", Chem. Pharm. Bull., vol. 49, No. 4, pp. 424–436 (2001).

Chemical Anstracts No. 131:299374v, Chemical Abstracts, vol. 131, No. 22, 1999, p. 546.

Primary Examiner—Alan L. Rotman
Assistant Examiner—Raymond Covington
(74) Attorney, Agent, or Firm—Greenblum & Bernstein, P.L.C.

(57) ABSTRACT

A novel benzamide derivative represented by the following general formula:

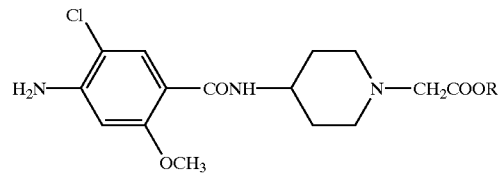

wherein R represents an alkyl group having 3 to 6 carbon atoms or a salt thereof, and a medicament comprising said derivative as an active ingredient. The medicament has excellent enhancing action on gastrointestinal tract motility, and is orally available with reduced side effects. Therefore, the medicament is extremely useful as an agent for therapeutic treatment of digestive diseases, an agent for improving function of gastrointestinal tract motility and the like.

24 Claims, No Drawings

BENZAMIDE DERIVATIVES AND DRUGS CONTAINING THE SAME

This application is a 371 of PCT/JP00/00560 filed Feb. 2, 2000.

FIELD OF THE INVENTION

The present invention relates to a novel benzamide derivative or a salt thereof which has an excellent enhancing effect on gastrointestinal tract motility and is useful as an agent for therapeutic treatment of digestive diseases, in particular, an agent for improving function of gastrointestinal tract motility.

BACKGROUND ART

Japanese Patent Unexamined Publication (Kokai) No. 5-262724/1993 filed by the present applicant discloses that 4-(4-amino-5-chloro-2-methoxybenzamido)-1-piperidineacetic acid and ethyl ester derivative thereof have enhancing actions on gastrointestinal tract functions (enhancing action on upper gastrointestinal tract motility and also enhancing action on lower gastrointestinal tract motility).

The aforementioned known compounds have been revealed to have enhancing actions on motility of upper gastrointestinal tract and lower gastrointestinal tract. However, 4-(4-amino-5-chloro-2-methoxybenzamido)-1-piperidineacetic acid has a problem of insufficient oral absorbability. Ethyl ester derivative thereof also has a problem from viewpoints of efficacy and safety, e.g., the derivative is not suitable for oral administration because it causes undesirable side effects such as vomiting. Accordingly, it has been desired to develop a medicament which has improved oral absorbability compared to 4-(4-amino-5-chloro-2-methoxybenzamido)-1-piperidine-acetic acid, and has reduced or no side effect such as those caused by the ethyl ester derivative thereof.

DISCLOSURE OF THE INVENTION

The inventors of the present invention conducted keen researches on the behavior of acetic acid esters of the aforementioned known benzamide derivative to solve the aforementioned problems. As a result, they found that novel benzamide derivatives of the present invention, i.e., ester derivatives of an alkyl having 3 to 6 carbon atoms that has a larger number of carbon atoms than that of the known benzamide derivative, had unexpectedly high enhancing effects on gastrointestinal tract motility. They also found that the emetic action caused by the ethyl ester derivative was reduced or eliminated in these compounds, and the compounds were extremely useful as an agent for therapeutic treatment of digestive diseases that can be administered orally, in particular, an agent for improving function of gastrointestinal tract motility such as a defecation stimulating agent. The present invention was achieved on the basis of these findings.

The present invention thus relates to novel compounds represented by the following general formula (I) or salts thereof:

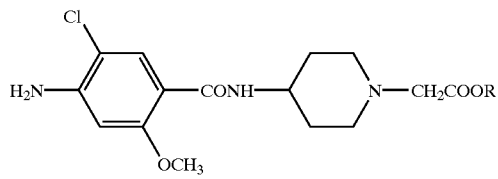

wherein R represents an alkyl group having 3 to 6 carbon atoms, preferably represents a straight or branched chain alkyl group having 3 to 6 carbon atoms.

According to preferred embodiments of the present invention, there are provided compounds represented by the aforementioned general formula (I) wherein R represents an alkyl group having 4 to 5 carbon atoms, preferably a straight or branched chain alkyl group having 4 to 5 carbon atoms. For example, those having n-butyl group or n-pentyl group as R are provided.

From another aspect of the present invention, there are provided medicaments comprising a compound represented by the aforementioned general formula (I) or a physiologically acceptable salt thereof as an active ingredient. The medicaments provided by the present invention are suitably used as, for example, a medicament for therapeutic and/or preventive treatment of digestive diseases, in particular, as a medicament for improving function of gastrointestinal tract motility.

From further aspect of the present invention, there are provided a use of a compound represented by the aforementioned general formula (I) or a physiologically acceptable salt thereof for the manufacture of the aforementioned medicaments; a method for therapeutic and/or preventive treatment of a digestive disease which comprises the step of administering to a mammal including a human a therapeutically and/or preventively effective amount of a compound represented by the aforementioned general formula (I) or a physiologically acceptable salt thereof; and a method for improving function of gastrointestinal tract motility which comprises the step of administering to a mammal including a human a therapeutically and/or preventively effective amount of a compound represented by the aforementioned general formula (I) or a physiologically acceptable salt thereof.

BEST MODE FOR CARRYING OUT THE INVENTION

In the aforementioned general formula (I) according to the present invention, the alkyl group having 3 to 6 carbon atoms represented by R may be straight, branched, cyclic, or a combination thereof, and preferably a straight or branched chain alkyl group. Examples of the alkyl group having 3 to 6 carbon atoms include, for example, n-propyl group, isopropyl group, cyclopropyl group, n-butyl group, isobutyl group, sec-butyl group, tert-butyl group, cyclobutyl group, cyclopropylmethyl group, n-pentyl group, isopentyl group, neopentyl group, tert-pentyl group, 1-cyclopropylethyl group, 2-cyclopropylethyl group, 2-methylcyclopropylmethyl group, cyclobutylmethyl group, n-hexyl group, isohexyl group, cyclopentylmethyl group and the like. Examples of the straight or branched chain alkyl group include, for example, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group and the like.

The compounds represented by the aforementioned general formula (I) according to the present invention may be converted into salts, preferably physiologically acceptable salts, as required. The produced salts may further be converted into free base compounds. Examples of the salts of the compounds according to the present invention include acid addition salts. Examples include salts with mineral acids such as hydrochloric acid, hydrobromic acid, hydroiodic acid, sulfuric acid, nitric acid, and phosphoric acid, salts with organic acids such as formic acid, acetic acid, propionic acid, butyric acid, valeric acid, pivalic acid, trifluoroacetic acid, acrylic acid, oleic acid, maleic acid, fumaric acid, citric acid, oxalic acid, succinic acid, tartaric acid, malic acid, malonic acid, lactic acid, glutaric acid, sebacic acid, gluconic acid, lauric acid, stearic acid, undecanoic acid, mandelic acid, methanesulfonic acid, ethanesulfonic acid, benzenesulfonic acid, benzoic acid, phthalic acid, cinnamic acid, p-toluenesulfonic acid, nicotinic acid, picric acid, adipic acid, aspartic acid, glutamic acid, 10-camphorsulfonic acid, optically active substances thereof and the like.

The compounds represented by the aforementioned general formula (I) or salts thereof according to the present invention may exist as any crystal forms depending on manufacturing conditions, and they may also exist any hydrates or solvates. The crystal forms, hydrates, solvates, and mixtures thereof also fall within the scope of the present invention. In addition, the compounds represented by the aforementioned general formula (I) according to the present invention may have one or more asymmetric carbon atoms depending on type of R. Any optically active compounds or diastereomers based on one or more asymmetric carbon atoms, any mixtures thereof or racemates fall within the scope of the present invention.

Specific examples of the compounds represented by the aforementioned general formula (I) according to the present invention include the following compounds and salts thereof. However, the present invention is not limited to these examples.

(1) n-Propyl 4-(4-amino-5-chloro-2-methoxybenzamido)-1-piperidineacetate
(2) Isopropyl 4-(4-amino-5-chloro-2-methoxybenzamido)-1-piperidineacetate
(3) n-Butyl 4-(4-amino-5-chloro-2-methoxybenzamido)-1-piperidineacetate
(4) Isobutyl 4-(4-amino-5-chloro-2-methoxybenzamido)-1-piperidineacetate
(5) n-Pentyl 4-(4-amino-5-chloro-2-methoxybenzamido)-1-piperidineacetate
(6) Isopentyl 4-(4-amino-5-chloro-2-methoxybenzamido)-1-piperidineacetate
(7) n-Hexyl 4-(4-amino-5-chloro-2-methoxybenzamido)-1-piperidineacetate
(8) Isohexyl 4-(4-amino-5-chloro-2-methoxybenzamido)-1-piperidineacetate Preferred compounds of the present invention include the following compounds.

(1) n-Butyl 4-(4-amino-5-chloro-2-methoxybenzamido)-1-piperidineacetate
(2) n-Pentyl 4-(4-amino-5-chloro-2-methoxybenzamido)-1-piperidineacetate The compounds represented by the aforementioned general formula (I) of the present invention can be prepared, for example, by the methods explained below. However, the methods for preparing the compounds are not limited to these methods.

According to the first embodiment of preparation of the compounds of the present invention, a compound represented by the aforementioned general formula (I) can be prepared by allowing an amine compound represented by the following formula (II):

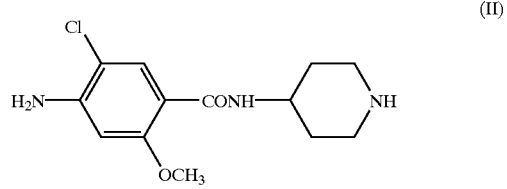

(II)

to react in a solvent in the presence of a base with a compound represented by the following general formula (III):

X—CH$_2$COOR (III)

wherein R has the same meaning as that defined above, and X represents a halogen atom or a leaving group such as p-toluenesulfonyloxy group and methanesulfonyloxy group.

The solvents used in the preparation may be any solvents so long as they does not inhibit the reaction. Examples include alcoholic solvents such as methanol, ethanol, isopropanol, tert-butanol, and 2-methoxyethanol, aromatic hydrocarbonic solvents such as benzene, toluene, and xylene, aprotic polar solvents such as ethyl acetate, acetone, tetrahydrofuran, 1,4-dioxane, acetonitrile, N,N-dimethylformamide, and dimethyl sulfoxide and the like. Examples of the base used include, for example, inorganic bases such as sodium carbonate, potassium carbonate, sodium hydrogencarbonate, and potassium hydrogencarbonate and the like. The reaction may be performed within a temperature range of from room temperature to a refluxing temperature of a solvent.

According to the second embodiment of preparation of the compounds of the present invention, a compound represented by the aforementioned general formula (I) can be prepared by allowing a carboxylic acid compound represented by the following formula (IV):

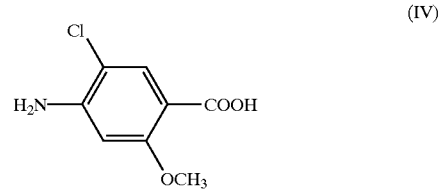

(IV)

to react with a carboxylic acid activator in a conventional manner to convert the carboxylic acid into an acid chloride, mixed acid anhydride or the like, and then allowing the resulting product to react in a solvent in the presence or absence of a base with an amine compound represented by the following general formula (V):

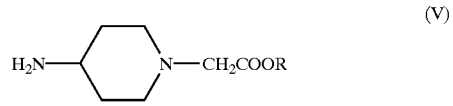

(V)

wherein R has the same meaning as that defined above.

Examples of the carboxylic acid activator used in the above preparation include, for example, thionyl chloride, oxalyl chloride, ethyl chloroformate, pivaloyl chloride, 1,1'-carbonyldiimidazole, 1,3-dicyclohexylcarbodiimide, propylphosphonic acid anhydride and the like. The solvents used may be any solvents so long as they does not inhibit the reaction. Examples include halogenated hydrocarbonic solvents such as methylene chloride, chloroform, and 1,2-dichloroethane, aromatic hydrocarbonic solvents such as benzene, toluene, and xylene, aprotic polar solvents such as ethyl acetate, acetone, tetrahydrofuran, 1,4-dioxane, acetonitrile, N,N-dimethylformamide, and dimethyl sulfoxide and the like. Example of the base used include, for example, organic bases such as triethylamine, N,N-diisopropyl-ethylamine, 1,8-diazabicyclo[5.4.0]-7-undecene, pyridine, and 4-dimethylamino-pyridine, inorganic bases such as sodium carbonate, potassium carbonate, sodium hydrogencarbonate, and potassium hydrogencarbonate and the like. The reaction may be performed within a temperature range of from 0° C. to a refluxing temperature of a solvent.

According to the third embodiment of preparation of the compounds of the present invention, a compound represented by the aforementioned general formula (I) can be prepared by allowing a carboxylic acid compound represented by the following formula (VI):

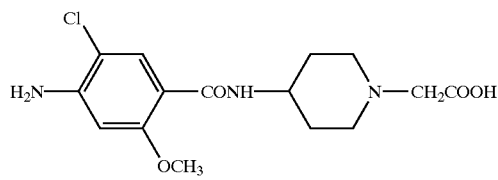

(VI)

to react in a solvent in the presence of a base with a compound represented by the following general formula (VII):

Y—R (VII)

wherein R has the same meaning as that defined above, and Y represents a halogen atom or a leaving group such as p-toluenesulfonyloxy group and methanesulfonyloxy group.

The solvents used in the preparation may be any solvents so long as they do not inhibit the reaction. Examples include aprotic polar solvents such as ethyl acetate, tetrahydrofuran, 1,4-dioxane, N,N-dimethylformamide, and dimethyl sulfoxide and the like. Example of the base used include, for example, inorganic bases such as sodium hydride, sodium hydroxide, potassium hydroxide, sodium carbonate, potassium carbonate, sodium hydrogencarbonate, and potassium hydrogencarbonate, and organic bases such as triethylamine, N,N-diisopropylethylamine, sodium methoxide, sodium ethoxide, 1,8-diazabicyclo[5.4.0]-7-undecene and the like. The reaction may be performed within a temperature range of from 0° C. to a refluxing temperature of a solvent.

According to the fourth embodiment of preparation of the compounds of the present invention, a compound represented by the aforementioned general formula (I) can be prepared by allowing a carboxylic acid compound represented by the aforementioned formula (VI) to react in the presence of an acid catalyst with an alcohol compound represented by the following general formula (VIII):

HO—R (VIII)

wherein R has the same meaning as that defined above.

Examples of the acid catalyst used in the preparation include, for example, hydrogen chloride, sulfuric acid, methanesulfonic acid, p-toluenesulfonic acid and the like. The alcohol compound represented by the aforementioned general formula (VIII) is used in a large excess amount so that it can also serve as a reaction solvent. The reaction is performed within a temperature range of from room temperature to a refluxing temperature of a solvent.

The starting materials used for the preparation of the compounds of the present invention are known compounds with a few exceptions. As for novel compounds, their preparations are described as Reference Examples.

The medicaments comprising as an active ingredient the compound represented by the aforementioned general formula (I) or a physiologically acceptable salt thereof according to the present invention are generally administered as preparations for oral administration such as capsules, tablets, subtilized granules, granules, powders and syrups, or preparations for parenteral administration such as suppositories. These preparations can be manufactured in a conventional manner by adding one or more of pharmacologically or pharmaceutically acceptable additives to the compound represented by the aforementioned general formula (I) or a physiologically acceptable salt thereof according to the present invention. As the pharmacologically or pharmaceutically acceptable additives used for preparations for oral administration or suppositories, additives for pharmaceutical preparations such as, for example, excipients such as lactose, D-mannitol, sucrose, corn starch, and crystalline cellulose; disintegrators such as carboxymethylcellulose, calcium carboxymethylcellulose, partly pregelatinized starch, croscarmellose sodium, and crospovidone; binders such as hydroxypropylcellulose, hydroxypropylmethylcellulose, and polyvinylpyrrolidone; lubricants such as magnesium stearate, talc, hydrogenated oil, dimethylpolysiloxane, hydrated silicon dioxide, colloidal silicon dioxide, and carnauba wax; plasticizers such as triethyl citrate, fatty acid glycerin esters, and polyethylene glycol; coating agents such as hydroxypropylmethylcellulose, sucrose, and titanium oxide; bases such as polyethylene glycol, and hard fat and the like may be used.

Doses of the medicament of the present invention may vary depending on symptoms or the age of a patient and the like. Generally, a dose for an adult in an amount of 0.1 to 500 mg for oral administration, or 0.01 to 300 mg for parenteral administration may be administered once or several times as divided portions in a day.

EXAMPLES

The present invention will be further explained with reference to the examples. However, the present invention is not limited to any specific details described in these examples.

Example 1 n-Butyl 4-(4-amino-5-chloro-2-methoxybenzamido)-1-piperidineacetate

Methanesulfonate

A mixture of 68.0 g of 4-(4-amino-5-chloro-2-methoxybenzamido)-1-piperidine-acetic acid, 27.5 g of potassium carbonate and 510 ml of dry N,N-dimethylformamide was stirred at 60° C. of outer temperature for 1.5 hours, and added dropwise with a solution of 22.4 ml of n-butyl bromide in 26 ml of dry N,N-dimethylformamide. The mixture was further stirred at the same temperature for 1.5 hours. The mixture was added with water, and extracted with ethyl acetate. The extract was washed successively with water and saturated aqueous sodium chloride solution, dried, and then the solvent was evaporated. The residue was added with n-heptane, and precipitated crystals were collected by filtration to obtain 57.6 g of colorless crystals. Methanesulfonate of the product was prepared in a conventional manner, and recrystallized from moist isopropanol to obtain colorless crystals (mp: 209–211.5° C).

Analysis for $C_{19}H_{28}ClN_3O_4 \cdot CH_4O_3S$;

| | |
|---|---|
| Calculated % | C, 48.63; H, 6.53; N, 8.51 |
| Found % | C, 48.37; H, 6.81; N, 8.44 |

In the same manner as described in Example 1, the compounds of Example 2 through 7 were obtained.

Example 2 n-Propyl 4-(4-amino-5-chloro-2-methoxybenzamido)-1-piperidineacetate Methanesulfonate Appearance: colorless needles (isopropanol) mp: 209–210° C.; Analysis for $C_{18}H_{26}ClN_3O_4 \cdot CH_4O_3S$;

| | |
|---|---|
| Calculated % | C, 47.54; H, 6.30; N, 8.75 |
| Found % | C, 47.47; H, 6.41; N, 8.69 |

Example 3

Isopropyl 4-(4-amino-5-chloro-2-methoxybenzamido)-1-piperidineacetate Hydrochloride Appearance: colorless needles (isopropanol); mp: 125–130° C.; Analysis for $C_{18}H_{26}ClN_3O_4 \cdot HCl \cdot 2H_2O$;

| | |
|---|---|
| Calculated % | C, 47.37; H, 6.85; N, 9.21 |
| Found % | C, 47.46; H, 6.67; N, 9.14 |

Example 4

Isobutyl 4-(4-amino-5-chloro-2-methoxybenzamido)-1-piperidineacetate Methanesulfonate Appearance: colorless needles (isopropanol); mp: 207–208° C.; Analysis for $C_{19}H_{28}ClN_3O_4 \cdot CH_4O_3S \cdot 1/4H_2O$;

| | |
|---|---|
| Calculated % | C, 48.19; H, 6.57; N, 8.43 |
| Found % | C, 48.14; H, 6.80; N, 8.36 |

Example 5 n-Pentyl 4-(4-amino-5-chloro-2-methoxybenzamido)-1-piperidineacetate <Methanesulfonate>

Appearance: colorless needles (isopropanol); mp: 202.5–203° C.; Analysis for $C_{20}H_{30}ClN_3O_4 \cdot CH_4O_3S$;

| | |
|---|---|
| Calculated % | C, 49.65; H, 6.75; N, 8.27 |
| Found % | C, 49.46; H, 6.98; N, 8.22 |

<L-Tartrate>

Appearance: colorless needles (isopropanol); mp: 155.5–156.5° C.; Analysis for $C_{20}H_{30}ClN_3O_4 \cdot C_4H_6O_6$;

| | |
|---|---|
| Calculated % | C, 51.29; H, 6.46; N, 7.48 |
| Found % | C, 51.13; H, 6.30; N, 7.40 |

Example 6

Isopentyl 4-(4-amino-5-chloro-2-methoxybenzamido)-1-piperidineacetate Methanesulfonate Appearance: colorless needles (isopropanol); mp: 199.5–201° C.; Analysis for $C_{20}H_{30}ClN_3O_4 \cdot CH_4O_3S \cdot 3/4H_2O$;

| | |
|---|---|
| Calculated % | C, 48.36; H, 6.86; N, 8.06 |
| Found % | C, 48.24; H, 6.64; N, 8.02 |

Example 7 n-Hexyl 4-(4-amino-5-chloro-2-methoxybenzamido)-1-piperidineacetate Hydrochloride Appearance: colorless plates (isopropanol); mp: 133–137° C.; Analysis for $C_{21}H_{32}ClN_3O_4 \cdot HCl \cdot 1/2H_2O$;

| | |
|---|---|
| Calculated % | C, 53.50; H, 7.27; N, 8.91 |
| Found % | C, 53.26; H, 7.27; N, 8.82 |

Example 8 n-Butyl 4-(4-amino-5-chloro-2-methoxybenzamido)-1-piperidineacetate Hydrochloride To a suspension of 5.00 g of 4-(4-amino-5-chloro-2-methoxybenzamido)-1-piperidineacetic acid in 75 ml of n-butanol, 1.80 g of sulfuric acid was added, and the mixture was refluxed for 3 hours. The solvent of the reaction mixture was evaporated, and the residue was adjusted to pH 9 to 10 by addition of aqueous potassium carbonate solution. Then, the mixture was extracted with methylene chloride. The extract was washed with saturated aqueous sodium chloride solution, dried, and then the solvent was evaporated. The residue was added with water, and adjusted to pH 2 with 10% hydrochloric acid. The precipitated crystals were collected by filtration, and washed successively with water and diisopropyl ether to obtain 5.51 g of pale yellow crystals. The crystals were recrystallized from n-butanol to obtain pale brown needles (mp: 133–136.5° C.). The crystals were further recrystallized from isopropanol to obtain colorless needles (mp: 141–144° C.).

Analysis for $C_{19}H_{28}ClN_3O_4 \cdot HCl \cdot H_2O$;

| | |
|---|---|
| Calculated % | C, 50.45; H, 6.91; N, 9.29 |
| Found % | C, 50.37; H, 6.58; N, 9.26 |

Reference Example 1 n-Butyl 4-tert-butoxycarbonylamino-1-piperidineacetate

A suspension of 1.00 g of 4-(tert-butoxycarbonylamino) piperidine and 0.72 ml of triethylamine in 6 ml of dry N,N-dimethylformamide was stirred at an inner temperature of 50° C., and added dropwise with a solution of 0.79 g of n-butyl chloroacetate in 4 ml of dry N,N-dimethylformamide. Stirring was continued at the same temperature for 1 hour. Then, the reaction mixture was added with water, and the precipitated crystals were collected by filtration. The crystals were washed successively with water and n-heptane to obtain 1.46 g of colorless scales (mp: 115.5–116.5° C.).

Analysis for $C_{16}H_{30}N_2O_4$;

| | |
|---|---|
| Calculated % | C, 61.12; H, 9.62; N, 8.91 |
| Found % | C, 60.90; H, 9.60; N, 8.88 |

Reference Example 2 n-Butyl 4-amino-1-piperidineacetate

A solution of hydrogen chloride in isopropanol (6 ml) was added to 1.35 g of n-butyl 4-tert-butoxycarbonylamino-1-piperidineacetate, and the mixture was stirred at room temperature for 15 minutes. The solvent was evaporated, and the residue was added with 5 ml of tetrahydrofuran and 1.3 ml of triethylamine. The precipitated solid was filtered off, and the solvent of the filtrate was evaporated to obtain 1.04 g of colorless oil.

Mass spectrum m/z: 214 (M+); IR spectrum ν (liq) cm$^{-1}$: 2960, 2940, 1746; NMR spectrum δ (CDCl$_3$) ppm: 0.93 (3H, t, J=7.5 Hz), 1.37 (2H, sex, J=7.5 Hz), 1.45–1.55 (2H, m), 1.55–1.65 (2H,m), 1.86 (2H, d, J=12 Hz), 2.02 (2H, brs), 2.20–2.30 (2H, m), 2.65–2.75 (1H, m), 2.90 (2H, d, J=12 Hz), 3.21 (2H, s), 4.12 (2H, t, J=7.5 Hz);

Example 9 n-Butyl 4-(4-amino-5-chloro-2-methoxybenzamido)-1-piperidineacetate

<Methanesulfonate>

To a suspension of 1065 g of 4-amino-5-chloro-2-methoxybenzoic acid in 11 L of dry tetrahydrofuran, 821 ml of triethylamine was added, and the mixture was stirred under ice cooling for 1 hour. The reaction mixture was added dropwise with 526 ml of ethyl chloroformate, and stirred under ice cooling for 1.5 hours. The reaction mixture was added with a solution of 1260 g of n-butyl 4-amino-1-piperidineacetate in 2.4 L of dry tetrahydrofuran, and stirred under ice cooling for 2 hours. The precipitated solid was filtered off, and the solvent of the filtrate was evaporated. The residue was added with aqueous potassium carbonate solution, and extracted with methyl isobutyl ketone. The extract was washed with saturated aqueous sodium chloride solution, dried, and then the solvent was evaporated. The residue was washed with diisopropyl ether to obtain 1759 g of colorless crystals (free base). Methanesulfonate of the product was prepared in a conventional manner, and recrystallized from moist isopropanol to obtain colorless crystals (mp: 209–211.5° C.). The compound obtained was identical to the compound obtained in Example 1 in IR spectrum and NMR spectrum.

Using the above-mentioned free base, the following acid addition salts were prepared in a conventional manner.

<Hydrobromide>

Appearance: colorless needles (isopropanol); mp: 198–201° C.; Analysis for $C_{19}H_{28}ClN_3O_4 \cdot HBr \cdot H_2O$;

| | |
|---|---|
| Calculated % | C, 45.93; H, 6.29; N, 8.46 |
| Found % | C, 45.85; H, 6.09; N, 8.41 |

<Nitrate>

Appearance: yellow prisms (isopropanol); mp: 168–170° C.; Analysis for $C_{19}H_{28}ClN_3O_4 \cdot HNO_3$;

| | |
|---|---|
| Calculated % | C, 49.51; H, 6.34; N 12.16 |
| Found % | C, 49.52; H, 6.20; N 12.10 |

<Sulfate>

Appearance: colorless needles (moist isopropanol); mp: 220–223° C. (decomposition); Analysis for $C_{19}H_{28}ClN_3O_4 \cdot H_2O_4S$;

| | |
|---|---|
| Calculated % | C, 46.01; H, 6.10; N, 8.47 |
| Found % | C, 45.99; H, 5.93; N, 8.38 |

<Phosphate>

Appearance: colorless needles (isopropanol); mp: 100–104° C.; Analysis for $C_{19}H_{28}ClN_3O_4 \cdot H_3O_4P \cdot 1/4H_2O$;

| | |
|---|---|
| Calculated % | C, 45.60; H, 6.35; N, 8.40 |
| Found % | C, 45.54; H, 6.08; N, 8.40 |

<Fumarate>

Appearance: colorless prisms (isopropanol); mp: 178–180° C.; Analysis for $C_{19}H_{28}ClN_3O_4 \cdot C_4H_4O_4$;

| | |
|---|---|
| Calculated % | C, 53.75; H, 6.28; N, 8.18 |
| Found % | C, 53.49; H, 6.09; N, 8.15 |

<Maleate>

Appearance: colorless prisms (isopropanol); mp: 124–126° C.; Analysis for $C_{19}H_{28}ClN_3O_4 \cdot C_4H_4O_4 \cdot 1/2H_2O$;

| | |
|---|---|
| Calculated % | C, 52.82; H, 6.36; N, 8.03 |
| Found % | C, 52.60; H, 6.19; N, 8.07 |

<p-Toluenesulfonate>
Appearance: colorless needles (isopropanol); mp: 208–211° C.; Analysis for $C_{19}H_{28}ClN_3O_4 \cdot C_7H_8O_3S$;

| | |
|---|---|
| Calculated % | C, 54.78; H, 6.36; N, 7.37 |
| Found % | C, 54.55; H, 6.34; N, 7.35 |

<L-Tartrate>
Appearance: colorless prisms (isopropanol); mp: 186–187° C. (decomposition); Analysis for $C_{19}H_{28}ClN_3O_4 \cdot C_4H_6O_6$;

| | |
|---|---|
| Calculated % | C, 50.41; H, 6.25; N, 7.67 |
| Found % | C, 50.14; H, 6.13; N, 7.57 |

<Malonate>
Appearance: colorless prisms (isopropanol-diisopropyl ether); mp: 105–106° C.; Analysis for $C_{19}H_{28}ClN_3O_4 \cdot C_3H_4O_4$;

| | |
|---|---|
| Calculated % | C, 51.71; H, 6.51; N, 8.08 |
| Found % | C, 51.41; H, 6.24; N, 8.18 |

<Succinate>
Appearance: colorless prisms (isopropanol-diisopropyl ether); mp: 110–111° C.; Analysis for $C_{19}H_{28}ClN_3O_4 \cdot C_4H_6O_4$;

| | |
|---|---|
| Calculated % | C, 53.54; H, 6.64; N, 8.14 |
| Found % | C, 53.34; H, 6.50; N, 8.11 |

<D-(+)-Malate>
Appearance: colorless prisms (isopropanol-diisopropyl ether); mp: 111–112° C.; Analysis for $C_{19}H_{28}ClN_3O_4 \cdot C_4H_6O_5$;

| | |
|---|---|
| Calculated % | C, 51.93; H, 6.44; N, 7.90 |
| Found % | C, 51.76; H, 6.28; N, 7.93 |

<L-(−)-Malate>
Appearance: colorless prisms (isopropanol-diisopropyl ether); mp: 111–112° C.; Analysis for $C_{19}H_{28}ClN_3O_4 \cdot C_4H_6O_5$;

| | |
|---|---|
| Calculated % | C, 51.93; H, 6.44; N, 7.90 |
| Found % | C, 51.71; H, 6.30; N, 7.87 |

Formulation Example 1 (Tablet)

The following ingredients were mixed in a conventional manner to manufacture a tablet.

| | |
|---|---|
| Compound of Example 1 (or 9) | 5 mg |
| Lactose | Sufficient Quantity |

-continued

| | |
|---|---|
| Corn starch | 15 mg |
| Polyvinylpyrrolidone | 2 mg |
| Magnesium stearate | 1 mg |
| Hydroxypropylmethylcellulose | 4 mg |
| Polyethyleneglycol | 0.5 mg |
| Titanium oxide | 0.5 mg |
| | 100 mg |

Formulation Example 2 (Capsule)

The following ingredients were mixed in a conventional manner, and filled into a hard capsule to manufacture a capsule.

| | |
|---|---|
| Compound of Example 9 | 10 mg |
| Lactose | Sufficient Quantity |
| Calcium carboxymethylcellulose | 5 mg |
| Hydroxypropylcellulose | 1 mg |
| Magnesium stearate | 1 mg |
| | 80 mg |

Formulation Example 3 (Powder)

The following ingredients were mixed in a conventional manner to manufacture powder.

| | |
|---|---|
| Compound of Example 9 | 10 mg |
| Lactose | Sufficient Quantity |
| D-Mannitol | 500 mg |
| Hydroxypropylcellulose | 20 mg |
| Talc | 2 mg |
| | 1000 mg |

Formulation Example 4 (Suppository)

The following ingredients were mixed in a conventional manner to manufacture a suppository.

| | |
|---|---|
| Compound of Example 9 | 5 mg |
| Hard Fat | 1295 mg |
| | 1300 mg |

Effects on colonic motility in conscious dogs are shown as examples demonstrating superior effects of compounds of the present invention, and test results demonstrating their emetic actions in ferrets are also shown as a side effect. The tested compound of Example 5 was used as a methanesulfonic acid salt, and the following compounds disclosed in Japanese Patent Unexamined Publication No. 5-262724/1993 were used as reference compounds:

Reference compound 1: 4-(4-amino-5-chloro-2-methoxybenzamido)-1-piperidineacetic acid hydrochloride, Reference compound 2: Ethyl 4-(4-amino-5-chloro-2-methoxybenzamido)-1-piperidine-acetate hydrochloride.

Test Example 1

Effect on Colonic Motility in Conscious Dogs

According to the method of Itoh et al. (Japanese J. Smooth Muscle Research, vol. 13, p.33, 1976; or Gastroenterologia Japonica, vol. 12, No 4, p.18, 1977) a strain-gauge force transducer was chronically sutured on ascending colon of beagle dogs of both sexes weighing 7.9 to 12.0 kg under general anesthesia in a direction that enabled measurement of circular muscle contractions of a portion of the ascending colon 10 cm distal from the cecum in the anus. A sailastic cannula was implanted in the duodenal wall to use as a catheter for intra-duodenal administration. After 2 weeks or more of the surgery, test compounds dissolved in saline containing 1% lactic acid were administered intra-duodenally (i.d.) to the beagle dogs 2 hours or more after feeding. Appearances of giant contractions in the ascending colon during 40 minutes after the administration were observed. The results are shown in Table 1.

TABLE 1

| Tested Compound | Number of tested dogs | Dose (mg/kg, i.d.) | Number of dogs showing colonic giant contraction |
|---|---|---|---|
| Control | 5 | 0 | 0 |
| Example 1 | 4 | 1.0 | 4 |
| Example 2 | 5 | 1.0 | 4 |
| Example 4 | 5 | 1.0 | 5 |
| Example 5 | 5 | 1.0 | 4 |
| Example 7 | 5 | 1.0 | 4 |
| Reference compound 1 | 5 | 1.0 | 0 |
| Reference compound 2 | 4 | 1.0 | 4 |

The compounds of the present invention exhibited extremely strong colonic contracting effect compared to the reference compound 1 by intra-duodenal administration, and almost comparable colonic contracting effect to that of the reference compound 2.

Test Example 2

Emetic Action in Ferrets

Each test compound dissolved in 10% aqueous dimethyl sulfoxide solution was administered to male ferrets, weighing 0.9 to 1.3 kg, and 16 hours fasting, and then the incidence of vomiting was observed during 2 hours after the administration. The results are shown in Table 2.

TABLE 2

| Tested Compound | Number of tested ferrets | Dose (mg/kg, p.o.) | Number of ferrets showing vomiting |
|---|---|---|---|
| Control | 8 | 0 | 0 |
| Example 1 | 8 | 10 | 0 |
| Example 2 | 8 | 10 | 2 |
| Example 4 | 8 | 10 | 1 |
| Example 5 | 8 | 10 | 0 |
| Example 7 | 8 | 10 | 1 |
| Reference compound 1 | 8 | 10 | 0 |
| Reference compound 2 | 8 | 10 | 8 |

Incidence of vomiting observed for orally administered reference compound 2 was not induced or very slightly induced by the compounds of the present invention.

Industrial Applicability

The novel benzamide derivatives or salts thereof have excellent enhancing effects on gastrointestinal tract motility and are orally available with reduced side effects, and accordingly, they are extremely useful as medicaments for therapeutic and/or preventive treatment of digestive diseases, or agents for improving function of gastrointestinal tract motility such as defecation stimulating agents.

What is claimed is:

1. A compound represented by the following general formula:

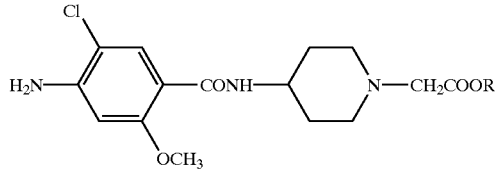

wherein R represent an alkyl group having 3 to 6 carbon atoms, or a physiologically acceptable salt thereof.

2. The compound or the salt thereof according to claim 1 wherein R is a straight or branched chain alkyl group having 3 to 6 carbon atoms.

3. The compound or the salt thereof according to claim 1 wherein R is a straight or branched chain alkyl group having 4 to 5 carbon atoms.

4. The compound or the salt thereof according to claim 1 wherein R is n-butyl group or n-pentyl group.

5. A composition which comprises a compound or a physiologically acceptable salt thereof according to claim 1 as an active ingredient.

6. A composition for improving function of gastrointestinal tract motility which comprises a compound or a physiologically acceptable salt thereof according to claim 1 as an active ingredient.

7. A method for therapeutic and/or preventive treatment of a digestive disease which comprises administering to a mammal a therapeutically and/or preventively effective amount of a compound or a physiologically acceptable salt thereof according to claim 1.

8. A method for improving function of gastrointestinal tract motility which comprises administering to a mammal a therapeutically and/or preventively effective amount of a compound or a physiologically acceptable salt thereof according to claim 1.

9. The composition according to claim 5 wherein R is a straight or branched chain alkyl group having 3 to 6 carbon atoms.

10. The composition according to claim 5 wherein R is a straight or branched chain alkyl group having 4 to 5 carbon atoms.

11. The composition according to claim 5 wherein R is n-butyl group or n-pentyl group.

12. The composition according to claim 6 wherein R is a straight or branched chain alkyl group having 3 to 6 carbon atoms.

13. The composition according to claim 6 wherein R is a straight or branched chain alkyl group having 4 to 5 carbon atoms.

14. The composition according to claim 6 wherein R is n-butyl group or n-pentyl group.

15. The method according to claim 7 wherein R is a straight or branched chain alkyl group having 3 to 6 carbon atoms.

16. The method according to claim 7 wherein R is a straight or branched chain alkyl group having 4 to 5 carbon atoms.

17. The method according to claim 7 wherein R is n-butyl group or n-pentyl group.

18. The method according to claim 7 wherein the mammal is a human.

19. The method according to claim 7 wherein the treatment comprises therapeutic treatment of a digestive disease.

20. The method according to claim 7 wherein the treatment comprises preventive treatment of a digestive disease.

21. The method according to claim 8 wherein R is a straight or branched chain alkyl group having 3 to 6 carbon atoms.

22. The method according to claim 8 wherein R is a straight or branched chain alkyl group having 4 to 5 carbon atoms.

23. The method according to claim 8 wherein R is n-butyl group or n-pentyl group.

24. The method according to claim 8 wherein the mammal is a human.

* * * * *